(12) United States Patent
Piancastelli

(10) Patent No.: US 12,377,021 B2
(45) Date of Patent: Aug. 5, 2025

(54) PERFORATING DEVICE

(71) Applicant: TEMA SINERGIE S.P.A., Ravenna (IT)

(72) Inventor: Stefano Piancastelli, Ravenna (IT)

(73) Assignee: TEMA SINERGIE S.P.A., Ravenna (IT)

( * ) Notice: Subject to any disclaimer, the term of this patent is extended or adjusted under 35 U.S.C. 154(b) by 0 days.

(21) Appl. No.: 18/871,508

(22) PCT Filed: Jun. 1, 2023

(86) PCT No.: PCT/IB2023/055649
§ 371 (c)(1),
(2) Date: Dec. 4, 2024

(87) PCT Pub. No.: WO2023/237981
PCT Pub. Date: Dec. 14, 2023

(65) Prior Publication Data
US 2025/0170023 A1    May 29, 2025

(30) Foreign Application Priority Data

Jun. 7, 2022  (IT) .................. 102022000011942

(51) Int. Cl.
| A61J 1/20 | (2006.01) |
| A61J 1/14 | (2023.01) |
| A61J 1/22 | (2006.01) |
| A61N 5/10 | (2006.01) |

(52) U.S. Cl.
CPC .......... *A61J 1/2013* (2015.05); *A61J 1/1406* (2013.01); *A61J 1/2048* (2015.05); *A61J 1/2051* (2015.05); *A61J 1/2082* (2015.05); *A61J 1/2089* (2013.01); *A61J 1/22* (2013.01); *A61N 5/1002* (2013.01); *A61N 2005/1021* (2013.01)

(58) Field of Classification Search
CPC ...... A61J 1/2013; A61J 1/1406; A61J 1/1412; A61J 1/1437; A61J 1/20; A61J 1/1013; A61J 1/2051; A61J 1/2065; A61J 1/2089
See application file for complete search history.

(56) References Cited

FOREIGN PATENT DOCUMENTS

| DE | 102017005791 A1 | 12/2018 |
| WO | 03051761 A2 | 6/2003 |
| WO | 2012061359 A1 | 5/2012 |
| WO | 2014020414 A1 | 2/2014 |
| WO | 2017172364 A1 | 10/2017 |

*Primary Examiner* — Leslie R Deak
(74) *Attorney, Agent, or Firm* — Bayramoglu Law Offices LLC

(57) ABSTRACT

Double-needle perforating device for bottles containing a medical liquid and provided with a pierceable closing septum, including a linear guide element, a kit slidable along the guide, at least two perforation needles integral with the movement of the slidable kit for the passage of the medical liquid and a second fluid, a needle lock element movable between a needle locking position and an access position which allows the passage of the needles in response to a longitudinal sliding of the kit along the guide.

9 Claims, 13 Drawing Sheets

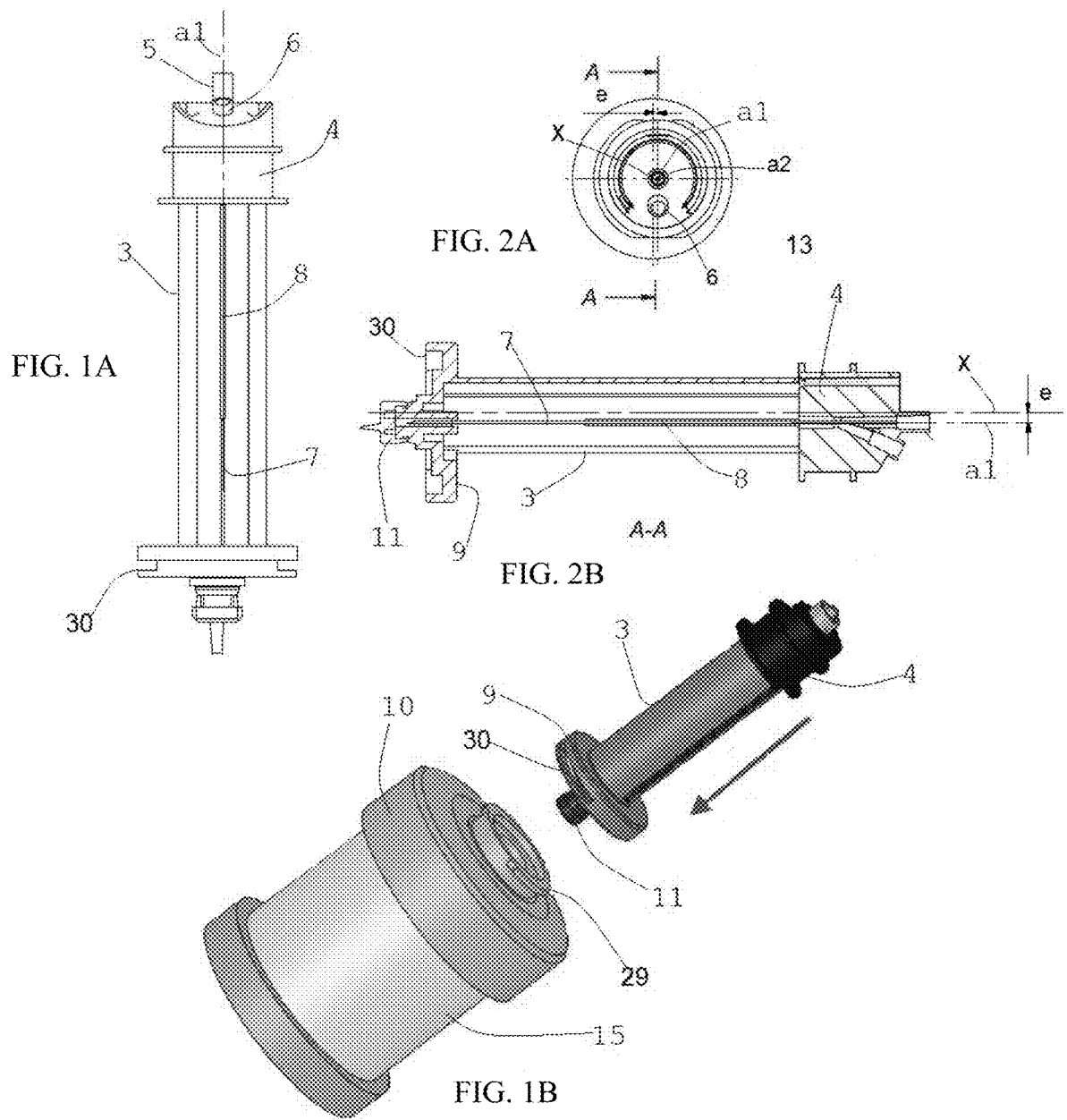

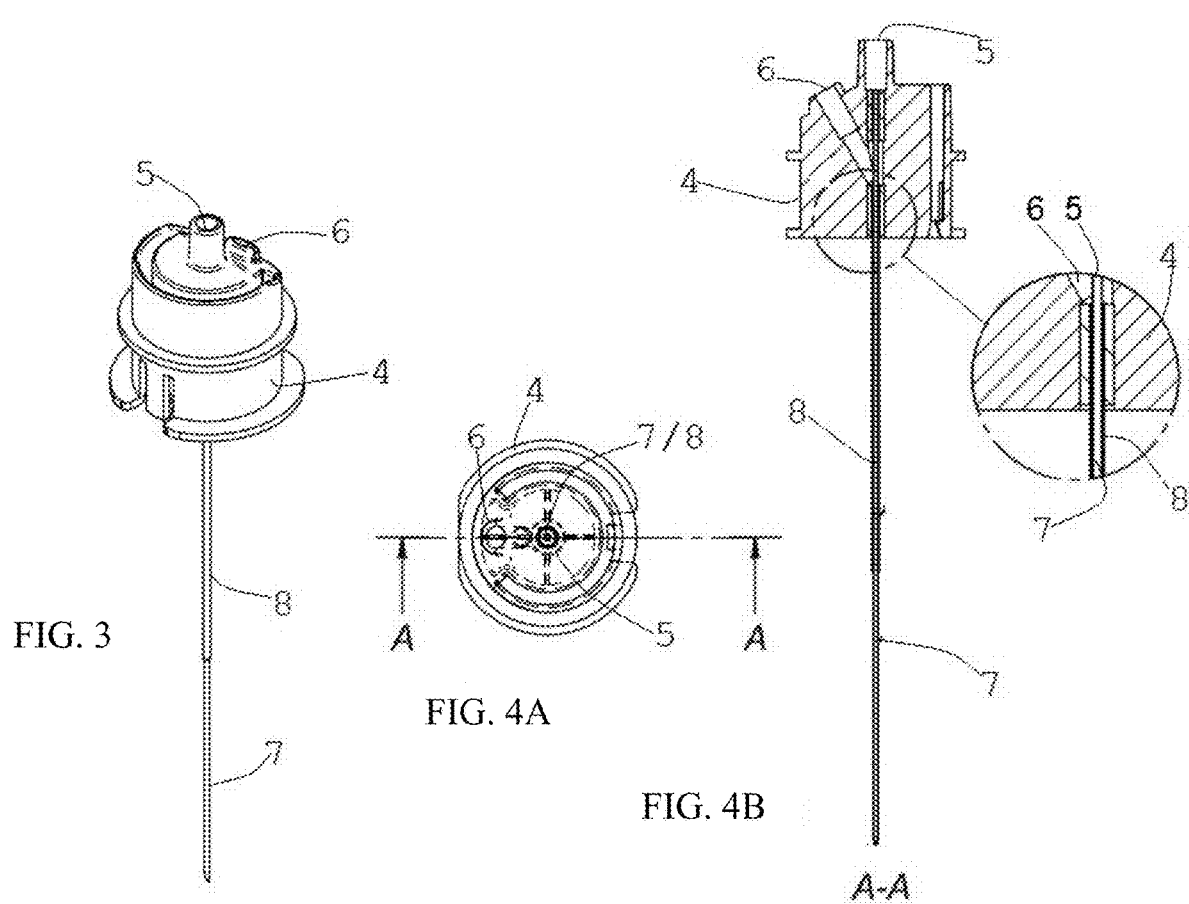

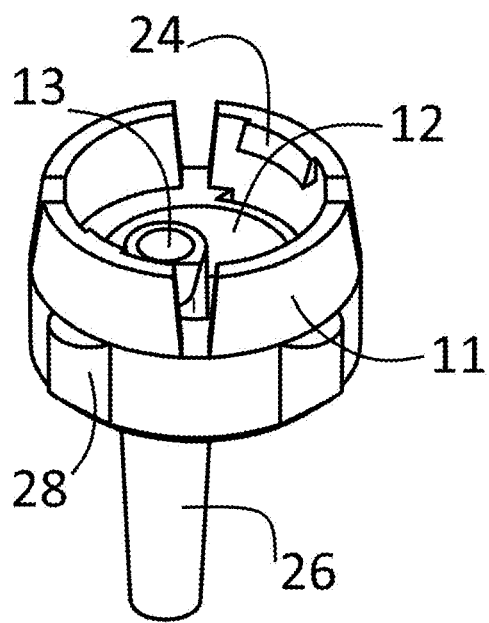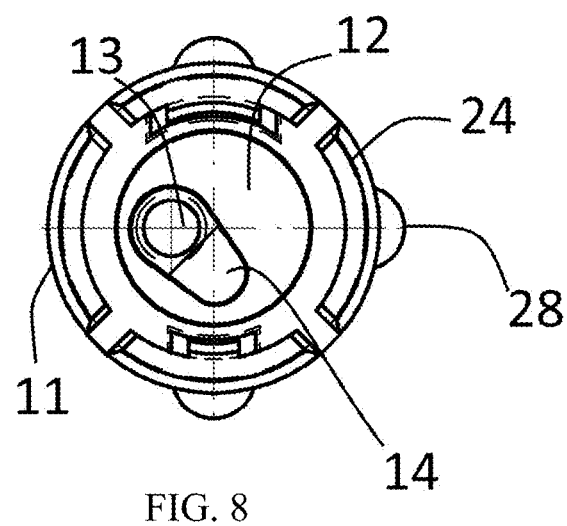
FIG. 7
FIG. 8

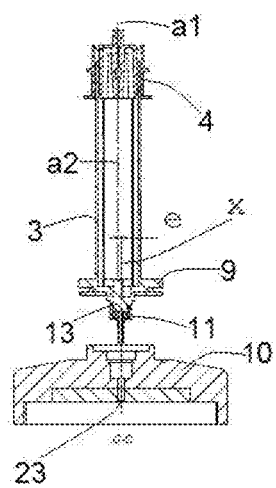
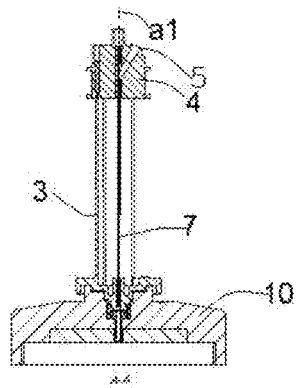
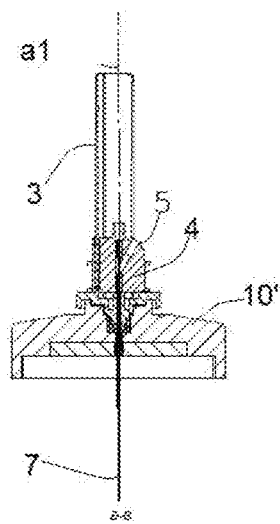
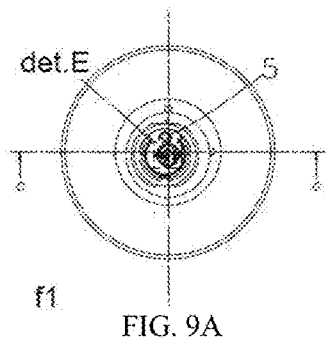
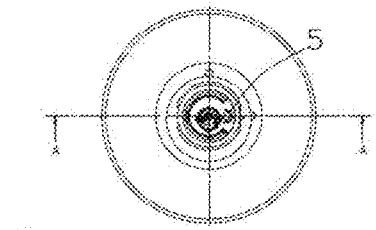
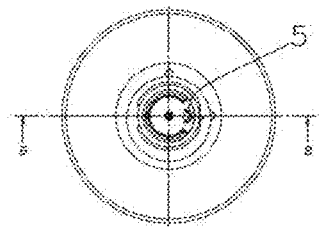
FIG. 9A  FIG. 9B  FIG. 9C Det.E

PERFORATING DEVICE

CROSS-REFERENCE TO THE RELATED APPLICATIONS

This application is the national phase entry of International Application No. PCT/IB2023/055649, filed on Jun. 1, 2023, which is based upon and claims priority to Italian Patent Application No. 102022000011942, filed on Jun. 7, 2022, the entire contents of which are incorporated herein by reference.

TECHNICAL FIELD

The invention relates to a perforating device, and in particular to a double-needle perforating device for the safe emptying of bottles of incoming medical liquids in shielded containers, for example radiopharmaceuticals, intended to be divided into bottles or syringes or directly infused into patients or for the collection of radioisotopes from incoming bottles in shielded containers.

BACKGROUND

At present, needle piercers are known which are applicable to bottles provided with a pierceable septum, in which a kit carrying a needle can be operated to perforate the septum, putting the inside of the bottle in communication with an external system, for example an infusion system of the medical liquid contained in the bottle.

A double-needle perforating device is known from WO2012061359 for filling and venting a bottle sealed by an elastomeric septum. This device comprises a collar for fixing to the bottle and a kit carrying two needles, movable within a guide channel aligned with the pierceable septum. In this solution, the needle holder kit is movable between a detached position and a position in which the needles pierce the septum, once reached, which the needle holder remains fixed to the guide channel to be able to be removed from the bottle.

A device is known from WO2014020414 for filling containers having a pierceable closing membrane, the device comprising a first portion associable with the container and a second portion carrying the needles which is movable between a detached position and a perforation position and recognition means for identifying the position of the second portion with respect to the first and making the two portions removably integral with the bottle.

However, such known systems have some drawbacks, in particular in relation to the guarantee of radiation protection for the operator, the possibility of separating the perforating device from the bottle after use while maintaining safety conditions against accidental leakage of the liquid and against accidental piercing of the operator.

SUMMARY

A first object of the invention is to propose a perforating device which overcomes the drawbacks of the known solutions and allows to safely and without losses empty bottles containing liquids, for example medical liquids, for example radiopharmaceuticals.

A further object is to propose a radiopharmaceutical transfer system from shielded containers which is safe in use and adaptable to both bottles and shielded containers of different shape and type.

These and further objects and technical aims and advantages have been achieved according to the invention with a perforating device and a transfer system for radiopharmaceuticals according to at least one of the attached claims 1-8 and 9-10, respectively.

A first advantage obtained according to the invention essentially consists of the fact that the perforating device allows in a simple, fast and safe manner to connect a bottle to be emptied to a system for transferring the contents of the bottle, for example to send it as an infusion to a patient or for fractionation in other bottles or syringes.

A second advantage is that a radiopharmaceutical transfer system according to the invention is of flexible use, adaptable to existing commercial bottles and safe for the operator both against losses of biological and radioactive liquid upon detachment of the perforating device from the bottle of liquid or radiopharmaceutical and against accidental piercing.

A further advantage is the better radiation protection obtained in the handling of containers containing radioactive liquids.

BRIEF DESCRIPTION OF THE DRAWINGS

These and other advantages will be better understood by anyone skilled in the art from the description below and the accompanying drawings, given as non-limiting example, in which:

FIG. 1A shows a perforating device according to the invention in raised side view;

FIG. 1B shows a perforating device according to the invention in exploded configuration with respect to a shielded container associated in use with the perforating device;

FIG. 2A shows the perforating device of FIG. 1A in a top view;

FIG. 2B shows the section A-A of the perforating device of FIG. 2A;

FIG. 3 shows a needle assembly of the perforating device of FIG. 1A in a raised side view;

FIG. 4A shows the needle holder assembly of FIG. 3 in top view;

FIG. 4B shows the section A-A of the needle holder assembly of FIG. 4A;

FIG. 7 shows a detail of the perforating device head seal of FIG. 1A in raised perspective view;

FIG. 8 shows the seal of FIG. 7 in top view;

FIGS. 9A-9D show a detail of a preferred embodiment of the locking/unlocking mechanism of the device of the invention;

DETAILED DESCRIPTION OF THE EMBODIMENTS

With reference to the attached drawings, a preferred embodiment of a double-needle perforating device according to the invention is described by way of example for safely emptying bottles 1 of medical liquids of the type provided with a pierceable closing section 2.

Figure 5:
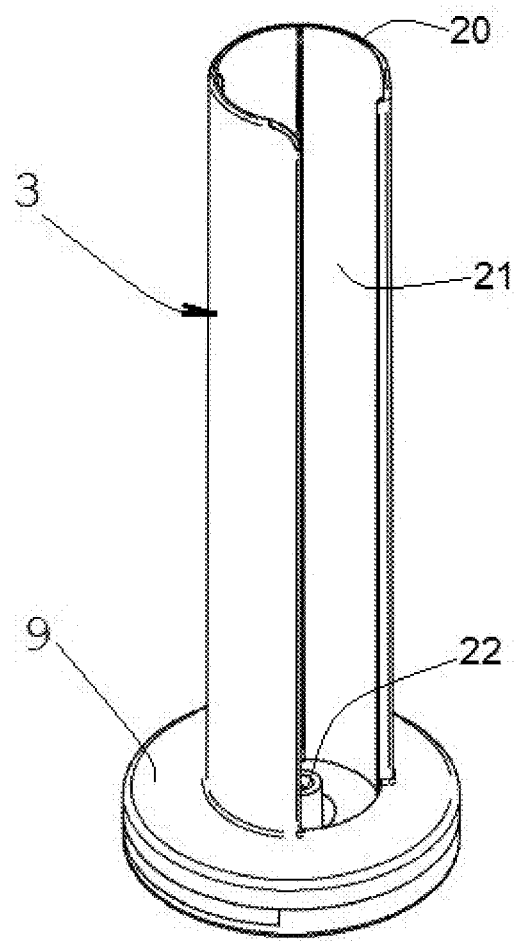
FIG. 5 shows a detail of the cylindrical body of the perforating device of FIG. 1A in perspective view.
Figure 6:
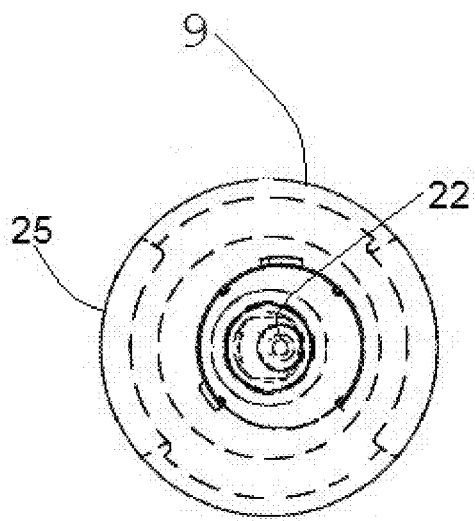
FIG. 6 shows the cylindrical body of FIG. 5 in top view.

The device (FIGS. 5, 6) comprises a linear guide element 3, preferably formed by a cylinder 20 of longitudinal axis x, open along a longitudinal slot 21 and emerging from an end flange 9 with fixing function to a connector element 10 (FIG. 10A) which in use is superimposed precisely on the septum 2 of the bottle 1.

Both the flange 9 and the connector 10 are therefore provided with respective holes 22, 23 configured to allow the passage of said perforation needles.

Along the guide 3 a kit 4 can slide (detail in FIGS. 3, 4A) provided with at least two accesses 5, 6 for connection to respective fluid lines 15, 16, (better visible in FIGS. 9A-9C) for the transfer of the medical liquid and of a second fluid, for example saline, by means of two perforation needles 7, 8 communicating with the accesses 5, 6 and integral with the movement of the kit 4, of which a first needle 7 is arranged for the passage of the medical liquid and the second needle 8 for the passage of the second fluid.

Preferably, the first and second needle 7, 8 are coaxial needles fixed to the kit 4 so that the inner needle, of greater length, communicates with a central access 5, while the outer concentric needle 8 forms a gap with the inner needle 7 communicating with the lateral access 6, thus creating two separate flow lines.

According to the invention, the device comprises a needle lock element 11, better visible in FIGS. 7,8, movably mounted on the guide element 3 and provided with an abutment surface 12 for preventing the passage of the needles and with a hole 13 instead adapted to pass the needles.

Figure 9D:
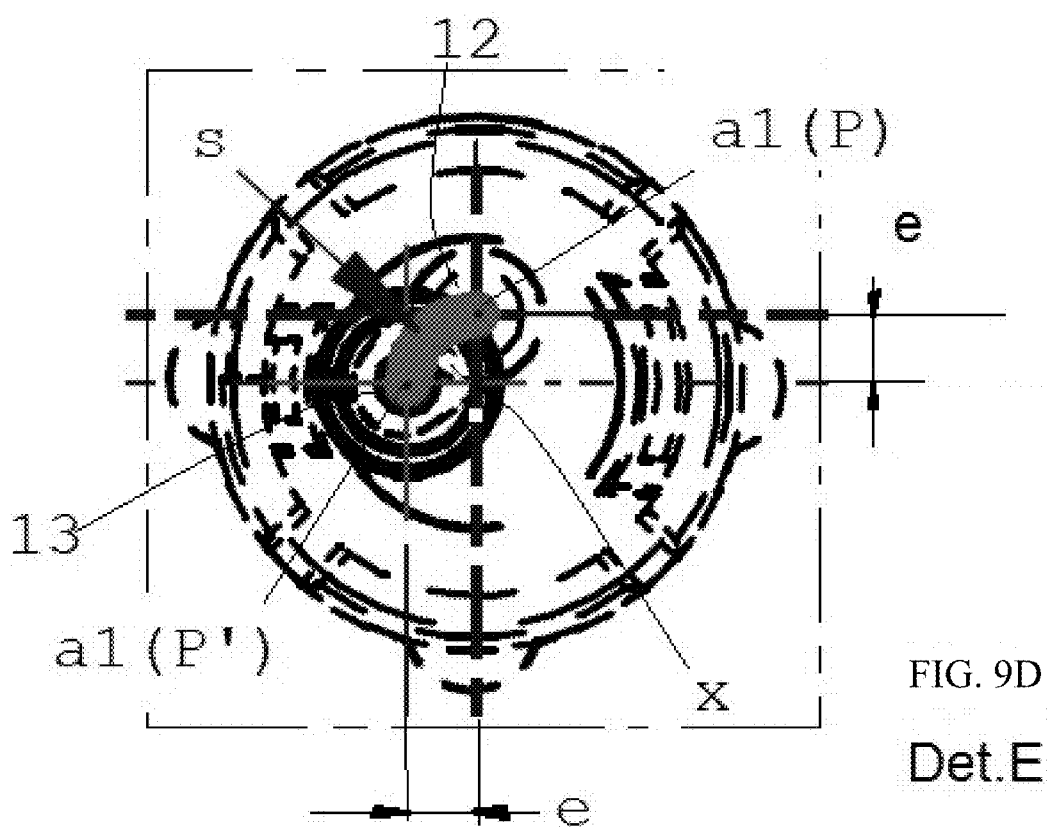
Figure 10A:
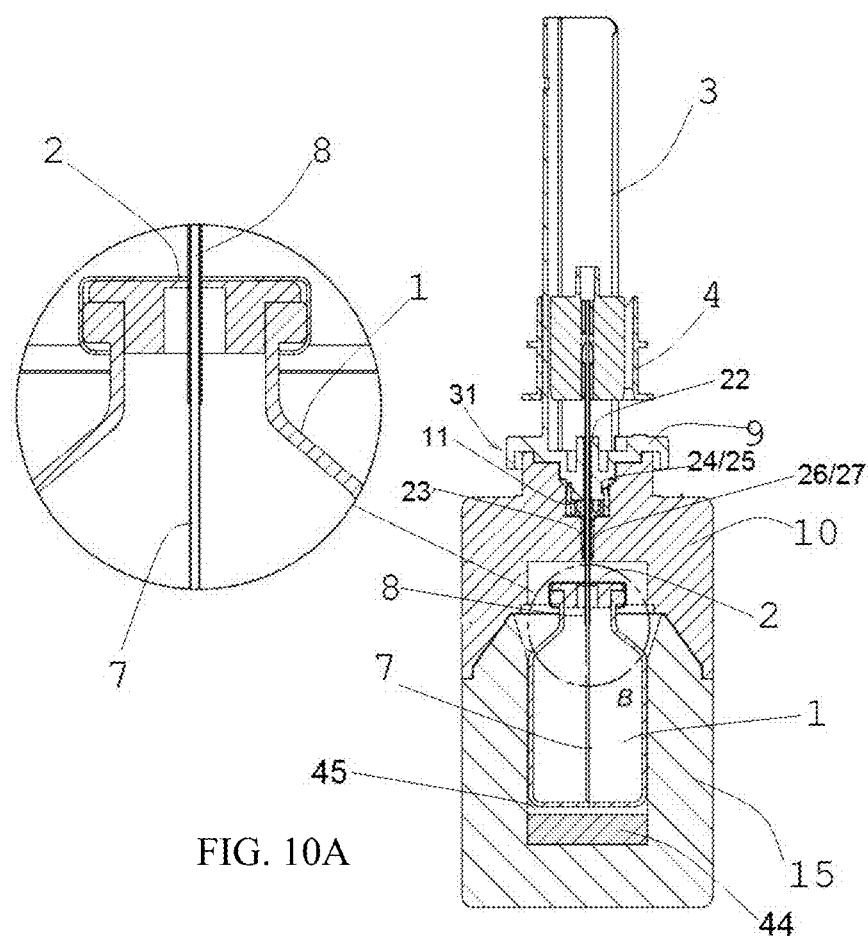
FIG. 10A shows a perforating device according to the invention associated with a shielded container for radiopharmaceuticals.

Advantageously, as better depicted in FIGS. 9A-9C, the needle lock 11 is rotatably movable with respect to the guide element 3 and to the flange 9 to pass from a locking position in which the abutment surface 12 is aligned with the sliding axis al' of the perforation needles to an access position, shown in FIG. 10A, in which instead the hole 13 is aligned with the sliding axis al of the needles and allows the passage thereof in response to a longitudinal sliding of the kit 4 along the guide 3.

In the example embodiment illustrated, the passage of the device from the locked position to the operative passage position of the needles is obtained by providing that the needle block 11 can rotate around the longitudinal axis x of the cylindrical guide 3 while the sliding axis al of the needles 7, 8, the hole 22 and the hole 13 are eccentric by the same measurement "e" with respect to the axis al so that in the permitted passage position they correspond and are aligned.

In the described example, in fact, the needle lock 11 has peripheral tabs 24 insertable in an outer collar 25 of the flange 9 which prevent the axial detachment but allow the relative rotation between lock 11 and guide 3, while below, the lock 11 extends with a projection 26 and with protrusions 28 capable of engaging in a univocal position in a seat 27 of the connector 10, so as to make the lock 11 and the connector 10 integral in rotation.

In greater detail and with reference to FIGS. 9A-9C, the locking/unlocking mechanism with eccentric movement of the device of the invention is described.

In step f1 the perforating device is in the extracted position, not engaged with the lid 10 and the sliding axis of the needle 7, better visible in FIG. 9D, is in the eccentric position al (P) and spaced by a distance "e" from the axis x axially coincident with the locking surface 12.

In step f2 the perforating device is fixed to the cover 10 and has been rotated by 90°. As a result of the rotation, while the lock 11 remains stationary, the flange 9 and the guide element rotate, dragging the needle-holder kit 4, anchoring to the lid 10 and the needle axis 7 makes a movement "s" corresponding, in the described example, to an arc equal to a quarter of a circle.

As a result of the relative rotation, the axis of the needles assumes the longitudinal position al (P') in which the sliding axis of the needles coincides with the hole 13 of the lock 11 and the hole 23 of the cover.

In step f3 the kit 4 is pushed downwards and the needle 7 can pass through the holes 13 and 23 to perforate the septum 2 of the bottle 1 (not shown).

Figure 11:
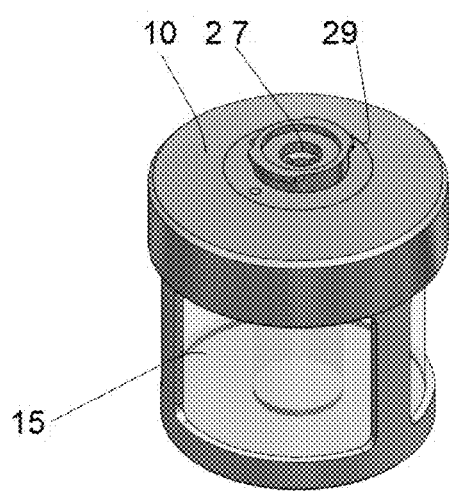
FIG. 11 shows a perspective view of a preferred embodiment of a shielded container for radiopharmaceuticals associable with the perforating device of the invention.
Figure 12A:
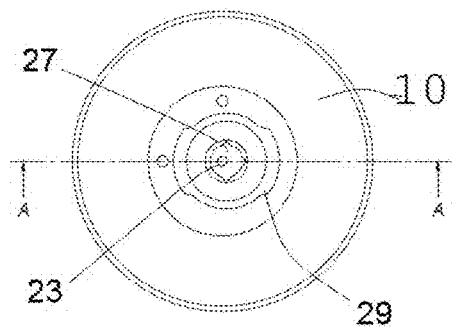
FIG. 12A shows the container of FIG. 11 in top view.
Figure 12B:
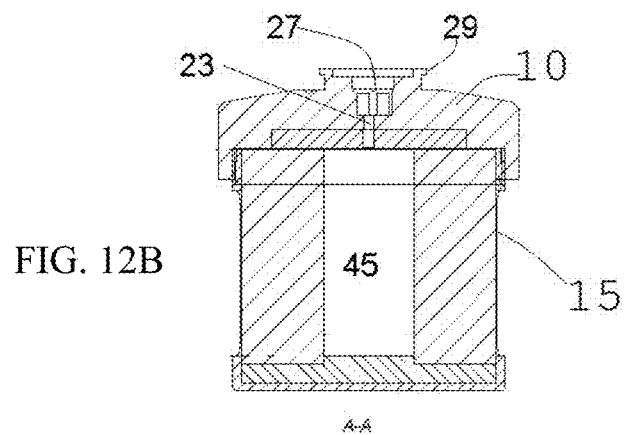
FIG. 12B shows the section A-A of the container of FIG. 12A.

FIGS. 11, 12A, 12B show an example of a connector 10 provided with a bayonet coupling 29 capable of engaging with a corresponding interlocking 30 present on the end portion 9 in order to obtain a stable and geometrically accurate reversible coupling 31 of the device, and in particular of the guide element 3 defining the sliding axis of the needles 7, 8 with the hole 23 of the connector.

It is understood, however, that the fixing of the guide element 3 to the connector 10 may be of a different type as long as it ensures the reversibility, stability and accuracy of the fixing in particular with respect to the longitudinal alignment.

Preferably, the connectors 10 are made of a shielding material and applied as lids to shielded containers 15 of the type used to house bottles 1 filled with radiopharmaceuticals in a shielded seat 45, but it is understood that the application of the perforating device can also be provided for liquids of a different nature.

However, it should be appreciated that, in the case of use with radiopharmaceuticals and therefore with shielded containers 15 and lids 10, the hole 23 constitutes the only unshielded point of the system during the application of the perforating device to the bottle 1, which represents a significant protection advantage of the operator in this specific application.

Figures 10B, 10C, 10D:
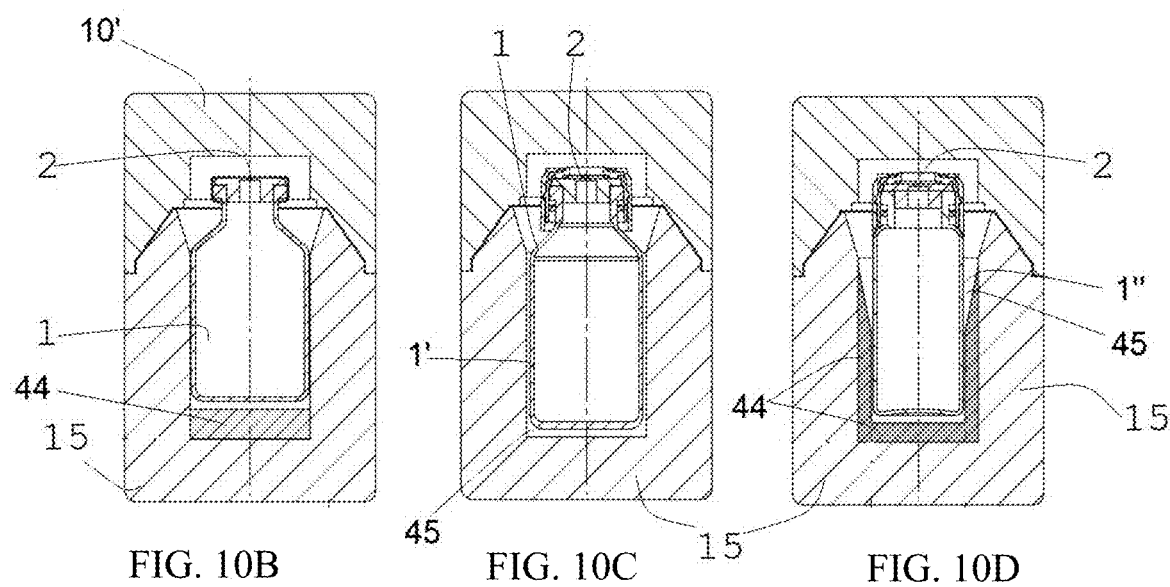
FIGS. 10B-10D show three examples of use of the container of FIG. 10A with different sized bottles for radiopharmaceuticals.

FIGS. 10B-10D show examples of use of bottles 1, 1', 1" of different shapes and sizes, housed in shielded containers 15 closed by lids 10', also shielded, to be replaced with special lids provided with holes similar to the lid 10 of FIG. 10A, in which to ensure the alignment with the sliding axis of the needle of the septum 2 of the bottles 1, 1', 1" the use of thicknesses 44 is provided to be arranged in the seat 45 of the container 15 housing the bottle, With the solution adopted, in the extracted condition from the connector 10 the needle lock 11 is in the non-operating locking position, in which the hole 13 is misaligned with respect to the hole 22 on the end portion 9 and instead coincides with the abutment surface 12 so that the double needle 7/8 is not mechanically capable of passing and remains in a safe position even with respect to possible accidental piercing of an operator.

Upon insertion of the device into a connector 10, the installation position is unique thanks to the protrusions 28 and/or the projection 26 present on the needle lock 11.

Once installed, i.e., inserted in the seat 27, the perforating device can be locked to the connector by rotating the flange 9 by an angle, for example 90°, preferably movable in only one permitted direction of rotation.

By effect of the rotation, the reversible coupling 31 stabilizes the guide element 3 which rotates with respect to the connector 10, while the needle lock 11 remains stationary in the seat 27 and, at the end of the stroke, the hole 22 of the portion 9 is aligned with the hole 13 in the lock 11 and the hole 23 in the connector lid 10, freeing the path for the descent of the needle which can slide together with the kit 4 until perforating the septum 2 of the bottle 1, with the needle 7 reaching the medical liquid.

Advantageously, during the use of the system, the needle 7/8 which passes through the hole 13 of the lock 11 also acts as a safety, locking any incorrect rotation between the body of the perforating device and the lock 11 itself which remains joined and fixed with respect to the connector 10, thus making it impossible to accidentally open the coupling 31 while the needle is inserted.

Figure 13:
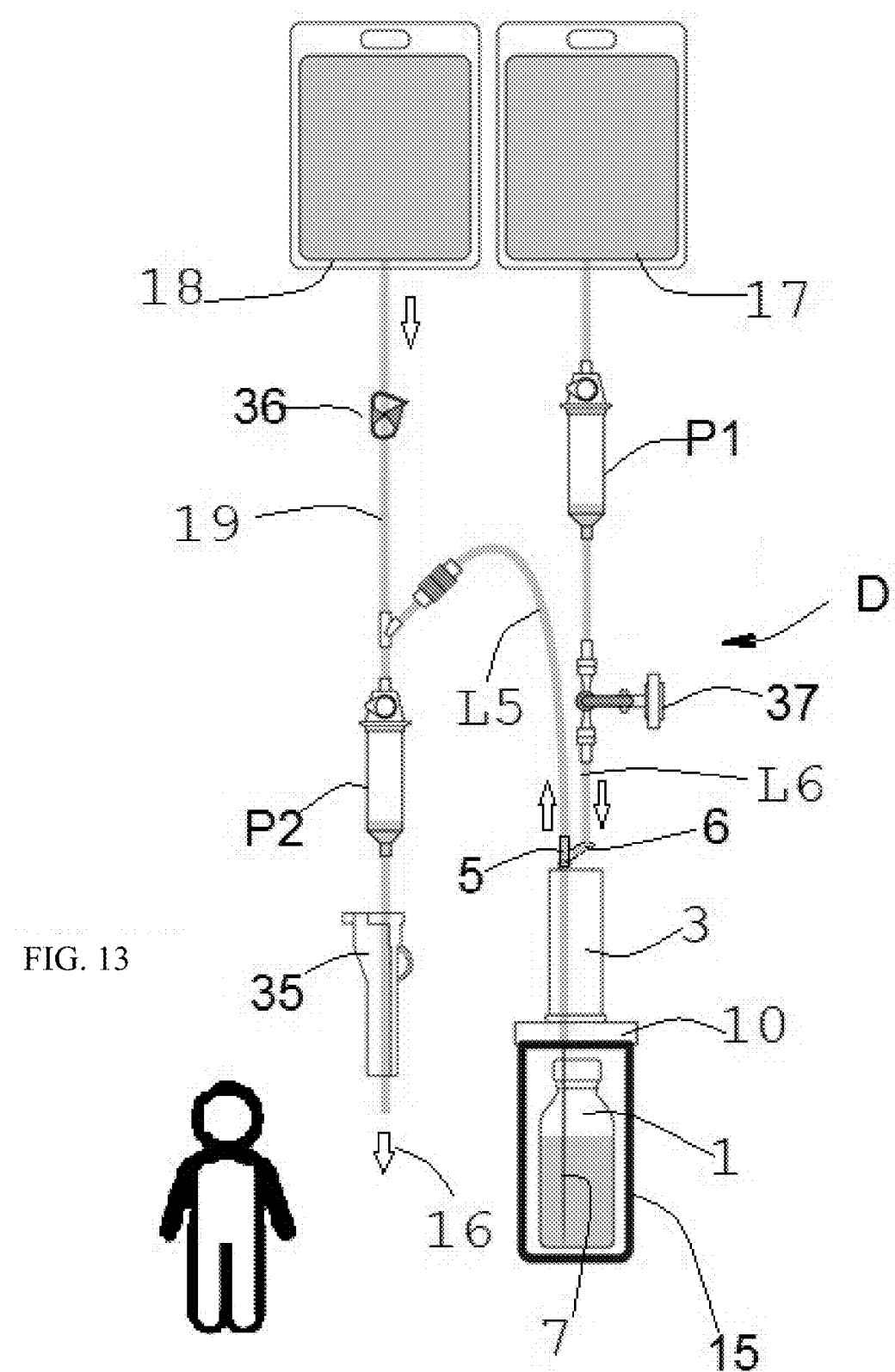
FIG. 13 shows a possible schematic of a disposable radiopharmaceutical transfer system according to the invention.

FIG. 13 schematically illustrates a disposable assembly D for the use of the device of the invention for emptying a bottle 1 and transferring the liquid to a liquid transfer point 16, for example for the infusion of the drug to a patient.

The assembly advantageously comprises a first fluid line L5 of the disposable type extended from the access 5 to the transfer point 16 and possibly comprising a connecting section 19 of the disposable type to a tank 18 of a further fluid, for example saline, of the liquid, and a second fluid line L6 of disposable type extended from the second access 6 to a source 17 of a second fluid, for example a saline solution tank.

In the example described, the line L5 comprises a chamber with dripper P2 for the transfer of the drug in addition to a flow regulator 35 and a choke 36 downstream of the tank 18, while the line L6 comprises a chamber with dripper P1 and a T-connector 37 provided with a filter.

It is intended, however, that the disposable assembly can be composed differently while comprising a perforating device and two disposable lines for the separate transfer of the medical fluid and the second fluid.

By way of example, with reference to FIGS. 14-16 and 17A-17F, a further preferred embodiment of a radiopharmaceutical transfer system comprising a perforating device according to the invention is described.

Figure 14:
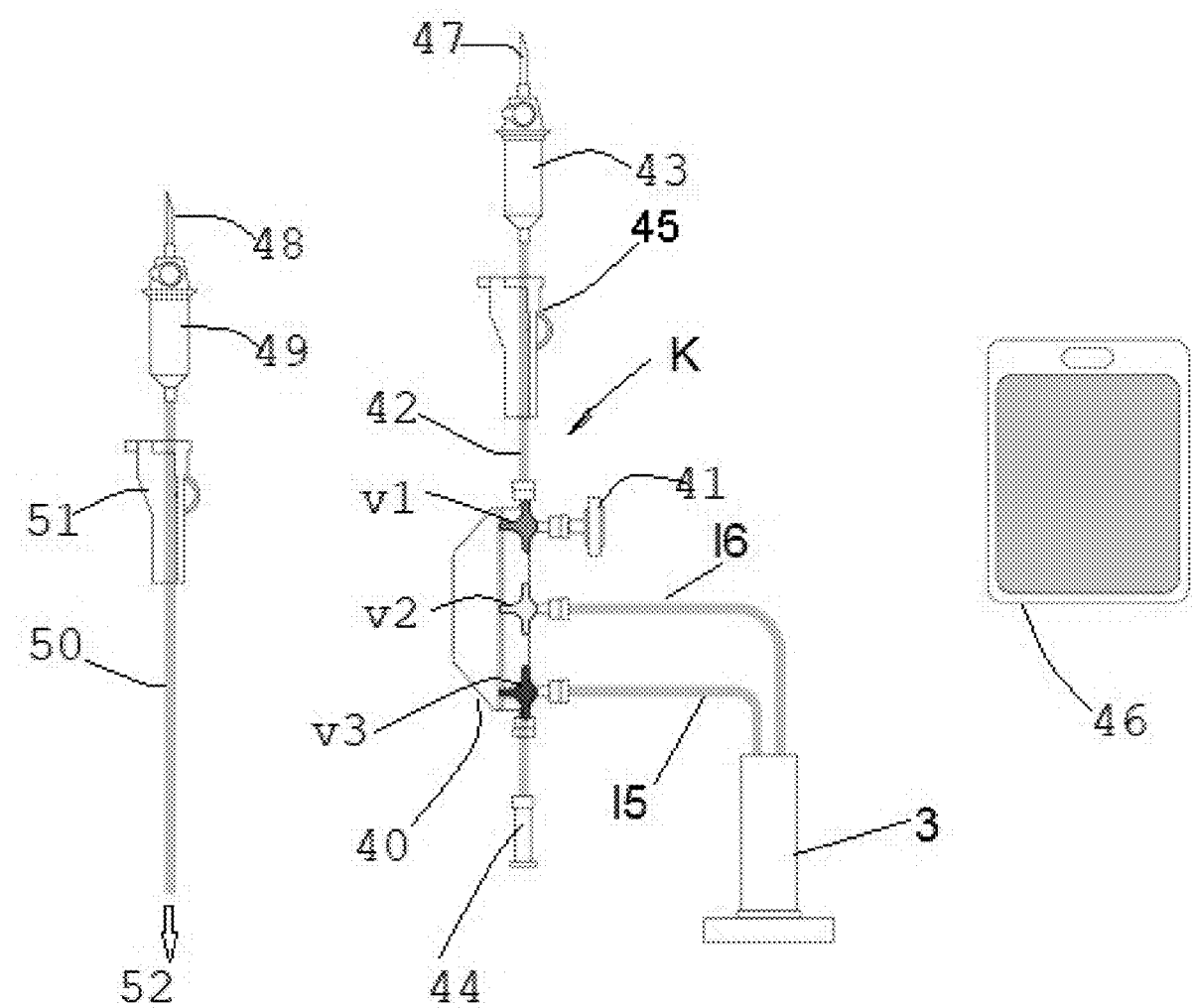
FIG. 14 shows the disposable components of a further disposable radiopharmaceutical transfer system according to the invention.

In the embodiment of FIG. 14, an assembly, or kit, K is described comprising a first pipe 42 extended between a dripper 43 provided with a piercer 47 for connecting to a tank 46 of a liquid such as saline, and an access 44 for a piercer 48 of a dripper 49 placed in input of a second infusion pipe 50, provided with a flow regulator 51 and intended for the infusion of liquid at a transfer point 52.

Along the first pipe 42 there is also a flow regulator 45 placed downstream of the dripper 43 and upstream of a manifold 40 on which three three-way valves V1-V3 are mounted in succession, of which the first v1 communicates with an aeration filter 41 the intermediate valve v2 communicates with the line 16 of the perforating device 3, and the third valve v3 communicates with the line 15 of the perforating device 3.

Figures 15, 16:
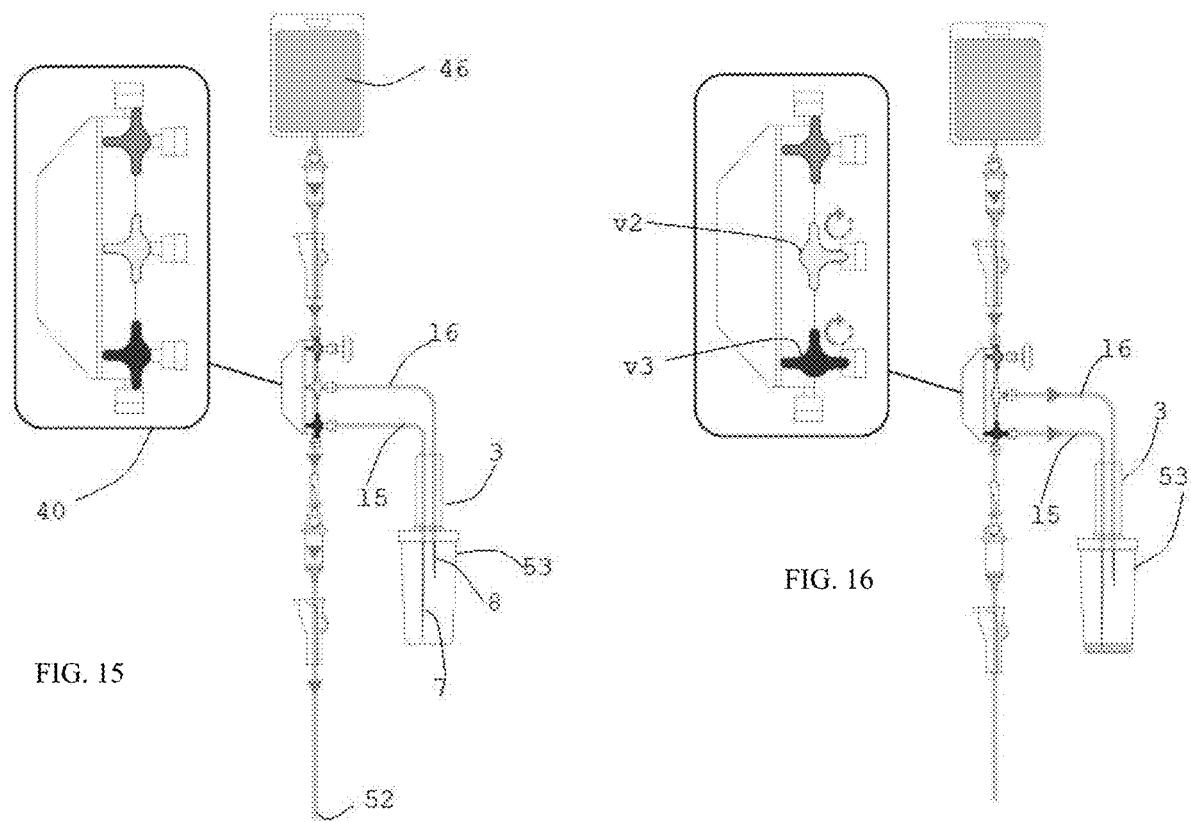
FIGS. 15 and 16 show the components of FIG. 14 in use configuration in a preliminary step of filling with saline, respectively of the flow lines arriving from the perforating device and for sending to the transfer point.

In FIG. 15 a first step of use of the kit K is schematically shown in which the needle 47 of the first pipe 42 has been connected with the saline tank 46 and the needle 48 of the second pipe 50 with the access 44 of the first pipe 42.

The perforating device 3 is applied to a cup 53 and is in the unlocking position.

In this step the valves v1-v3 are aligned along the line 42 and allow the passage of the solution from the tank 46 to the transfer point 52 and the filling of the second pipe 50.

FIG. 16 shows a second preparatory step in which the intermediate valve v2 and the third valve v3 are operated to allow the passage of the saline from the tank 46 to the needles 7, 8 of the perforating device and therefore the washing and filling with saline also of the first pipe 42.

It should be specified that in the diagram shown the needles 7, 8 are shown for better understanding as separate needles communicating with lines 15, 16, but which may be of the coaxial type described above.

In FIGS. 17A-17F the cup 53 has been removed and the perforating device is applied in the unlocked position to a container 15 of the type as described above.

In FIGS. 17A-17F the steps of an example using the kit K for the transfer of the liquid contained in the bottle 1 to the transfer point 52 by means of, for example, a peristaltic pump 55 are schematically shown in succession.

Figure 17A:
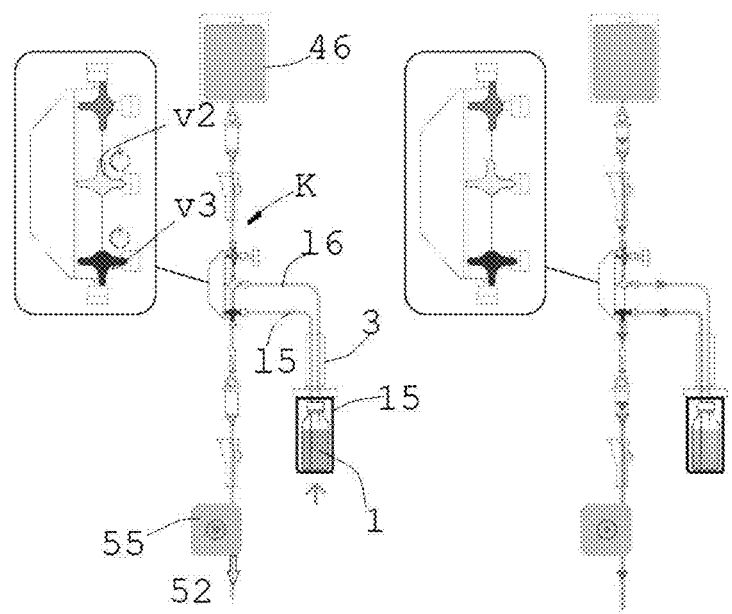
FIGS. 17A-17F show the subsequent steps of using the system of FIG. 14 with a perforating device according to the invention.
Figure 17B:
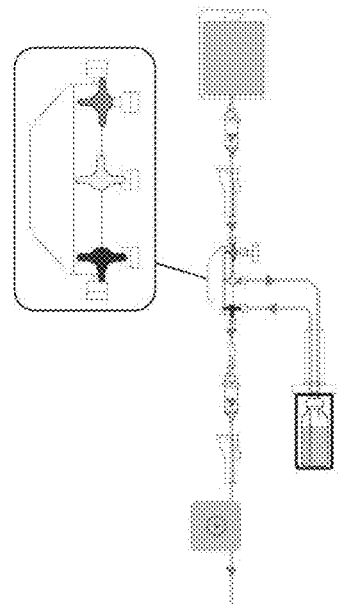

In FIG. 17A the valve v2 connects the tank 46 and the line 16, while the valve v3 connects the line 15 with the transfer point 52, so that the medical liquid of the bottle 1 is transferred to the point 52 and in the meantime the bottle 1 begins to fill with saline (FIG. 17B).

Figure 17C:
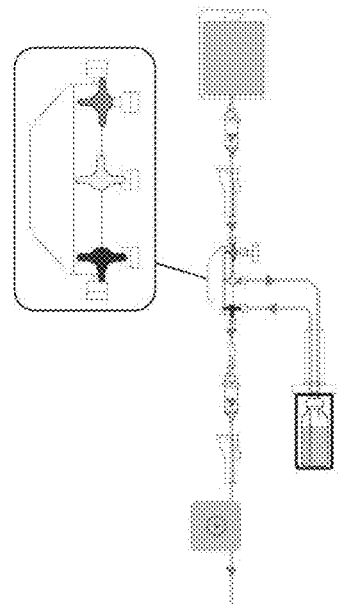

In FIG. 17C the transfer of medical fluid from the bottle is completed and the transfer of saline which enters the bottle from line 16 and exits from line 15 continues.

Figure 17D:
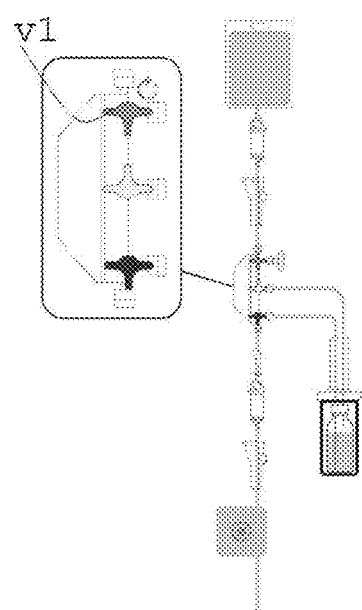
Figure 17E:
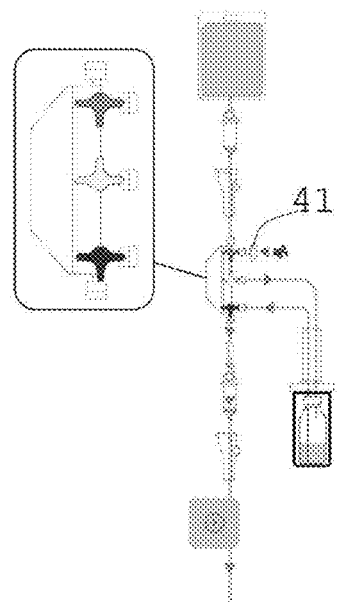
Figure 17F:
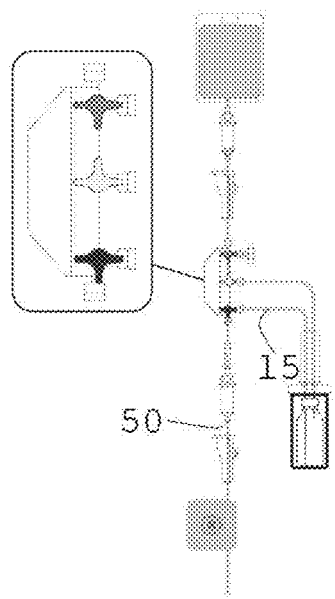

In FIG. 17D the first valve v1 excludes the tank 46 and allows the suction of air from the filter 41 (FIG. 17E) so that while the line 16 empties and air enters the bottle, the remaining saline contained in the bottle 1 is completely transferred to the point 52 also emptying the line 15 and the infusion pipe 50.

It is clear that the kit K allows to carry out the complete transfer and washing of all the parts affected by contact with the medical liquid and to therefore operate in absolute safety even in use with radiopharmaceuticals and the like.

At the end of the transfer of the drug, to unlock the device from the container 15 it is sufficient to lift the needle, retracting the kit 4, rotating the guide element in the opposite direction to the direction of installation, and then remove the perforating device.

In this position, the lock 11 is returned to the locked position with the surface 12 aligned with the needle and preventing it from leaking out, protecting the operator from accidental piercing injuries.

Furthermore, in a further advantageous aspect of the invention, the needle lock 11 comprises a concavity 14 adjacent to the hole 13 with the function of receiving and retaining a quantity of liquid possibly released from the perforation needle, keeping it inside the device and avoiding any risk of contamination, particularly serious in the case of radiopharmaceuticals.

The present invention has been described according to preferred embodiments, but equivalent variants can be conceived without departing from the scope of protection granted.

What is claimed is:

1. A double-needle perforating device for bottles containing a medical liquid and provided with a pierceable closing septum, comprising
a linear guide element of a longitudinal axis
a kit slidable along the longitudinal axis of the guide and provided with at least two accesses for connection to respective fluid lines for transfer of the medical fluid and/or a second fluid,
at least two perforation needles integral with a movement of the sliding kit, comprising a first needle for a passage of the medical liquid and a second needle for a passage of the second fluid, the first and second needles communicating respectively with the accesses and being movable along at least one sliding axis,
a needle lock element connected to the guide element and provided with
at least one abutment surface adapted to prevent the passage of the perforation needles and
at least a first hole adapted instead to allow the passage of the perforation needles,
the needle lock being movable to pass from a locking position in which an abutment surface is aligned with the perforation needles and prevents the passage thereof in response to a possible longitudinal sliding of the kit along the guide, to a permitted passage position in which the first hole is aligned with the sliding axis of the perforation needles and allows the passage thereof in response to a longitudinal sliding of the kit along the guide; wherein the needle lock can rotate around the longitudinal axis of the guide to move between the locking position and the permitted passage position.

2. The perforating device according to claim 1, wherein the first and second needles are coaxial needles.

3. The perforating device according to claim 1, wherein the needle lock comprises a concavity adjacent to the first hole adapted to receive and retain an amount of liquid released by at least one perforation needle.

4. The perforating device according to claim 1, wherein the sliding axis of the needles and the hole of the lock are eccentric with respect to the longitudinal axis of the guide by a same measurement.

5. The perforating device according to claim 1, comprising a fixing portion of the guide to a connector element associable with the perforating device, precisely overlappable on a pierceable septum of the bottle and comprising a hole to allow the passage of the perforation needles.

6. An assembly for a transfer of a radiopharmaceutical contained in a bottle, comprising at least one perforating device according to claim 1 and a connector comprising a hole to allow the passage of the perforation needles and precisely connectable to the perforating device by means of a reversible coupling, wherein the connector is a lid for shielded containers of radiopharmaceutical bottles housed in a seat of the container and is made of a shielding material.

7. The assembly according to claim 6, comprising at least one thickness to be arranged in the seat of the container which houses the bottle in order to ensure an alignment of the septum of the bottle with the hole of the lid.

8. A disposable assembly for a transfer of a liquid contained in a bottle, comprising the perforating device according to claim 1, provided with a first access connected to a first fluid line of the disposable type communicating at least with a transfer point of the liquid, and a second access connected to a second fluid line of the disposable type communicating at least with a tank of a second fluid, for example saline.

9. The assembly according to claim 8, comprising:
a first pipe extended between a dripper connectable to a tank of a second liquid to an access for a connection to a second infusion pipe at a transfer point
a manifold arranged along the first pipe on which three three-way valves are mounted in succession, of which a first communicates with an aeration filter, an intermediate valve communicates with the line of the access of the perforating device and a third valve communicates with the line of the second access of the perforating device.

* * * * *